(12) United States Patent
Pickhard

(10) Patent No.: US 7,611,491 B2
(45) Date of Patent: Nov. 3, 2009

(54) DEVICE FOR AUTOMATICALLY INJECTING LIQUIDS TO BE INJECTED

(75) Inventor: Ewald Pickhard, Grossebersdorf (AT)

(73) Assignee: Pharma Consult Ges.m.b.H. & Co NFG KG, Vienna (AT)

( * ) Notice: Subject to any disclaimer, the term of this patent is extended or adjusted under 35 U.S.C. 154(b) by 358 days.

(21) Appl. No.: 10/570,124

(22) PCT Filed: Aug. 27, 2004

(86) PCT No.: PCT/AT2004/000295

§ 371 (c)(1),
(2), (4) Date: Oct. 18, 2006

(87) PCT Pub. No.: WO2005/021070

PCT Pub. Date: Mar. 10, 2005

(65) Prior Publication Data

US 2007/0073232 A1    Mar. 29, 2007

(30) Foreign Application Priority Data

Aug. 29, 2003 (AT) ............................. GM 593/2003

(51) Int. Cl.
*A61M 5/00* (2006.01)
*A61M 5/20* (2006.01)
(52) U.S. Cl. .................. 604/139; 604/110; 604/136
(58) Field of Classification Search .............. 604/122, 604/139, 192, 155–157, 110, 136
See application file for complete search history.

(56) References Cited

U.S. PATENT DOCUMENTS 3,485,239 A * 12/1969 Vanderbeck ................ 604/192

(Continued)

FOREIGN PATENT DOCUMENTS

DE    363984    11/1922

(Continued)

*Primary Examiner*—Nicholas D Lucchesi
*Assistant Examiner*—Pritesh Patel
(74) *Attorney, Agent, or Firm*—Chapman and Cutler LLP

(57) ABSTRACT

In a device (1) for automatically injecting injection liquids, including an axially subdivided housing whose parts are connectable with each other, wherein an axially displaceable pressure pin (5) is guided in a first housing part (2), which pin is capable of being inserted against a force accumulator (6) and locked in the inserted position and extended upon relief of the force accumulator (6), wherein an injection needle (15) fixed in a needle guide (14) and an ampoule (13) are mounted in a second housing part (3) so as to be axially displaceable relative to each other, wherein the injection needle (15) on its side facing the ampoule (13) is designed as a perforation piece (32) for the ampoule (13), the ampoule (13) with its end facing the injection needle (15) is mounted to reach into a sleeve (16) fixed within the second housing part (3) and whose inner diameter substantially corresponds to the outer diameter of the ampoule (13). Radially inwardly protruding projections (17) are formed on the inner periphery of the sleeve (16), and the sleeve (16) comprises locking members cooperating with locking members (20) of the needle guide (14), whereby an axial displacement of the ampoule (13) in the direction to the needle guide (14) while overcoming the displacement resistance exerted by the projections (17) causes the release of the locking members (20) and the axial displaceability of the needle guide (14).

20 Claims, 8 Drawing Sheets

U.S. PATENT DOCUMENTS

| | | | |
|---|---|---|---|
| 3,742,948 A | | 7/1973 | Post et al. |
| 4,624,660 A | | 11/1986 | Mijers et al. |
| 5,042,977 A | | 8/1991 | Bechtold et al. |
| 5,273,544 A | * | 12/1993 | van der Wal ................ 604/134 |
| 5,378,240 A | * | 1/1995 | Curie et al. ................. 604/110 |
| 5,709,668 A | | 1/1998 | Wacks |
| 5,788,677 A | * | 8/1998 | Botich et al. ................ 604/195 |

FOREIGN PATENT DOCUMENTS

| | | |
|---|---|---|
| EP | 0 518 416 A1 | 12/1992 |
| WO | WO 01/07104 A1 | 2/2001 |
| WO | WO 0107104 A1 * | 2/2001 |

* cited by examiner

DEVICE FOR AUTOMATICALLY INJECTING LIQUIDS TO BE INJECTED

The invention relates to a device for automatically injecting injection liquids, including an axially subdivided housing whose parts are connectable with each other, wherein an axially displaceable pressure pin is guided in a first housing part, which pin is capable of being inserted against a force accumulator and locked in the inserted position and extended upon relief of the force accumulator, and an injection needle fixed in a needle guide and an ampoule are mounted in a second housing part so as to be axially displaceable relative to each other, wherein the injection needle on its side facing the ampoule is designed as a perforation piece for the ampoule.

Devices of the initially defined kind have become known under the name of autoinjector. The known devices are instruments which facilitate the injection of an emergency drug into the body in case of emergency. Autoinjectors are, for instance, used in allergic emergencies, e.g. after insect bites, snake bites etc., yet also in the military field, for instance, in order to quickly counteract intoxications by chemical warfare agents. The known devices in most cases are devised as disposable devices and, therefore, disposed of after one-time use.

From AT 303 251, an injection device is known, which comprises two housing parts capable of being screwed one into the other, an activator containing a spring-loadable pressure pin, and an injector containing the ampoule and the injection needle as an inseparable unit. After having been unlocked, the spring-loaded pressure pin exerts a force on the piston plug of the ampoule, whereupon the ampoule is, at first, displaced along with the injection needle in the axial direction within the injector housing so that the injection needle penetrates into the patient's body and the liquid contained in the ampoule is subsequently set under such a high pressure that a sealing membrane provided between the ampoule and the injection needle will break, thus causing the liquid to be ejected. That known configuration, however, involves the drawback that the broken membrane may obstruct the injection needle, thus preventing the rapid ejection of the injection liquid.

From WO 01/07104, an advanced injection device has already become known, in which the ampoule and the injection needle are arranged within the housing so as to be relatively displaceable in the axial direction, and the injection needle end facing the ampoule is designed as a perforation piece for the ampoule. The ampoule is, in fact, mounted in the interior of the housing without being firmly connected with the injection needle. It is only during application that the ampoule is displaced in the direction of the injection needle under the force of the pressure pin extending upon relief of the force accumulator and pierced by the injection needle end designed as a perforation piece.

The previously known autoinjectors, however, are only insufficiently able to meet the recent demands as are prescribed for use in the military field. Autoinjectors that are to be suitable for military purposes must, in fact, safeguard a longer-than-average storability and sterility of the respective injection devices and be designed extremely robust. On a trial basis, autoinjectors for military purposes are, for instance, dropped on a stone floor from a height of two meters in order to check whether the ampoule has broken or whether the mechanical impact has caused slipping of the ampoule and/or injection needle in a manner that the sealing disc of the ampoule is pierced by the injection needle. Similar tests are also carried out under extreme temperature conditions.

The invention aims to provide a device of the initially defined kind, which complies with the demands set out above for use in the military field in a satisfactory manner. To solve this object, the device according to the invention essentially consists in that the ampoule with its end facing the injection needle is mounted to reach into a sleeve fixed within the second housing part and whose inner diameter substantially corresponds to the outer diameter of the ampoule, that radially inwardly protruding projections are formed on the inner periphery of the sleeve, and that the sleeve comprises locking members cooperating with locking members of the needle guide, whereby an axial displacement of the ampoule in the direction to the needle guide while overcoming the displacement resistance exerted by the projections causes the release of the locking members and the axial displaceability of the needle guide. By the ampoule with its end facing the injection needle being mounted so as to reach into a sleeve fixed within the second housing part, the radially inwardly protruding projections provided on the inner periphery of the sleeve and defining a smaller diameter than the ampoule are able to prevent the ampoule from slipping in the direction to the injection needle. The energy set free by an impact or other mechanical action at worst is absorbed by the inwardly protruding projections while expanding the wall of the sleeve. After a short displacement, the ampoule will, thus, be stuck between the inwardly protruding projections with any further displacement being prevented.

In accordance with the invention, the sleeve is equipped with locking members which cooperate with respective locking members of the needle guide such that the needle guide too, along with the injection needle fixed therein, will be secured against axial displacement. Both the ampoule reaching into the sleeve and the needle guide connected with the sleeve are, hence, coupled to the sleeve, with the sleeve being, in turn, immovably retained in the second housing part, to which end the end-side annular sleeve surface facing the needle guide preferably rests on a radially inwardly protruding projection of the second housing part. This is to ensure that the ampoule or the needle guide will not be detached, and the injection needle will be unable to emerge from the injector housing, even if the injection device falls from an extreme height on hard ground.

To activate the injection device, it is provided according to the invention that an axial displacement of the ampoule in the direction to the needle guide while overcoming the displacement resistance exerted by the projections causes the release of the locking members and the axial displaceability of the needle guide. Thereby, the locking members will only be released if the ampoule in the injector housing is pushed towards the injection needle by the spring force of the unlocked pressure pin, whereby such high forces are released that the displacement resistance exerted on the ampoule by the projections of the sleeve will be overcome. The release of the locking members fixing the needle guide may advantageously be effected in that the locking members of the sleeve are formed on arms capable of excursing outwardly in a resilient manner, said arms each carrying an inwardly protruding projection in the region of their coupling site, which cooperates with the ampoule under the excursion of the arms and release of the locking members. In this case, the locking members may be comprised of snap-in noses engaging in reception openings. An axial displacement of the ampoule, thus, causes the ampoule to run up inwardly protruding projections formed on outwardly resilient arms in a manner that further axial displacement causes an excursion of the arms and the locking members formed on said arms to disengage and release the needle guide.

After having released the needle guide, the ampoule is able to pass through the sleeve unhampered and approach the injection needle end designed as a perforation piece. In order to cushion the hard impact of the ampoule on the injection needle to be expected subsequently, a spring element acting in the axial direction is preferably arranged between the needle guide and the ampoule. The spring action causes the absorption of the impact energy, thus preventing a possible fracture of the glass ampoule. The spring element may be designed in one piece with the needle guide, as a spring basket compressible in the axial direction such that the spring basket can be additionally used as a spacer in order to prevent the ampoule from striking against the bottom of the needle guide. The ampoule will consequently reach its end position closely in front of the bottom of the needle guide, whereby a rupture of the ampoule head will be safely prevented.

In order to prevent the injection liquid from escaping prematurely, the configuration is advantageously further developed such that the injection needle includes a radial passage opening at an axial distance from its end designed as a perforation piece for the ampoule. The channel of the injection needle, thus, will not enter into fluid connection with the injection liquid immediately upon piercing of the ampoule, but only after a further axial displacement which causes the radial passage opening of the injection needle to reach into the ampoule. In order to ensure that the injection liquid be pressed into the injection needle through the radial passage opening rather than emerging around the injection needle laterally from the pierced rubber sealing disc or the ampoule head, the configuration is preferably further developed such that the radial passage opening in the axial direction is arranged between the injection needle end designed as a perforation piece and an annular web arranged on the needle guide and surrounding the injection needle, said annular web defining a closed annular space between the web and the injection needle reaching into the ampoule.

In order to enhance the security against fracture of the ampoule, which is mostly made of glass, the configuration is preferably further developed such that the ampoule with its end facing away from the injection needle is arranged to reach into a sleeve-shaped ampoule socket which comprises a plurality of lamellar guide ribs extending in the longitudinal direction. In this case, the ampoule is positioned centrally within the sleeve-shaped ampoule socket. The elastic guide ribs of the ampoule socket protect the glass ampoule from fracture, since the vibrations acting on the injection device from outside are to the major extent absorbed by the guide ribs rather than transmitted to the ampoule. It is, thus, safeguarded that the glass ampoule is mounted in a fracture-proof manner even under heavy vibrations.

In order to ensure the required sterility, the ampoule reception opening facing the first housing part including the pressure pin is advantageously closed by a gas-permeable sealing foil. This gas-permeable sealing foil enables the interior of the fully equipped, bilaterally closed injection part to be sterilized by the aid of a gas so as to guarantee the sterility of the injection part over years. To provide complete tightness, a seal and, in particular, an O-ring seal may be arranged between the outer periphery of the ampoule socket and the inner periphery of the second housing part.

In the following, the invention will be explained in more detail by way of an exemplary embodiment schematically illustrated in the drawing. Therein:

Figure 1:
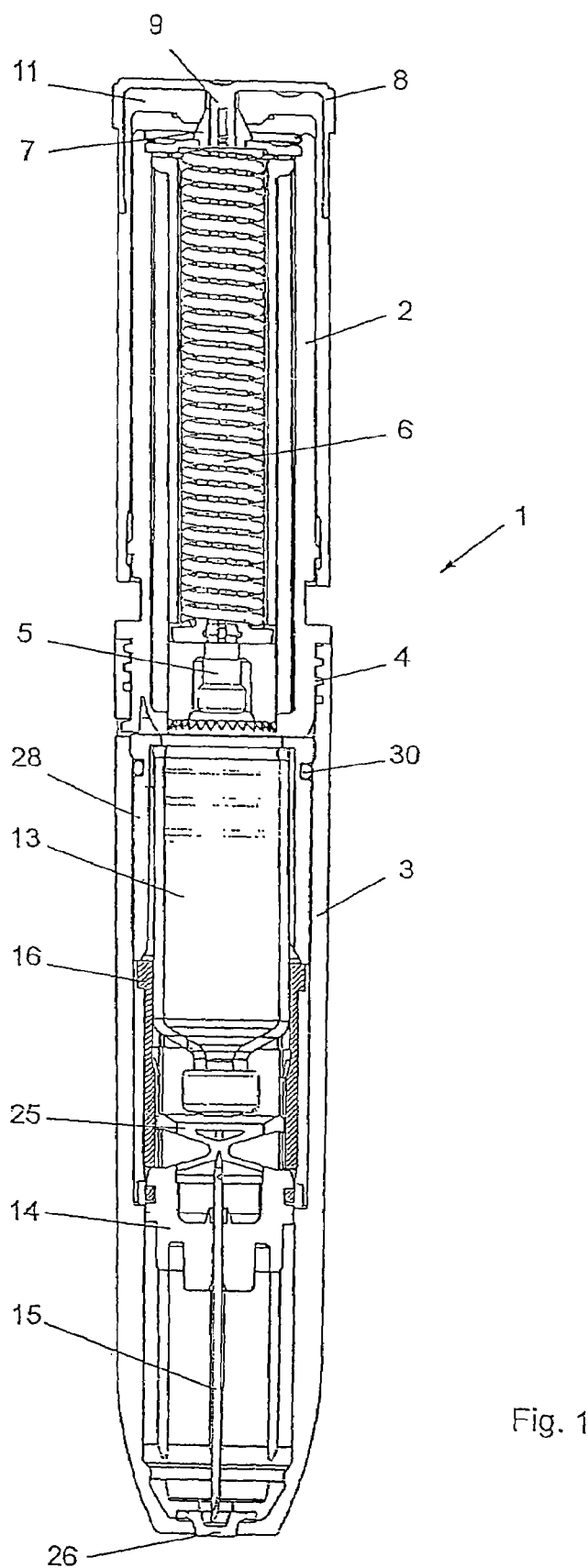
FIG. 1 depicts a longitudinal section through the device according to the invention.
Figure 2:
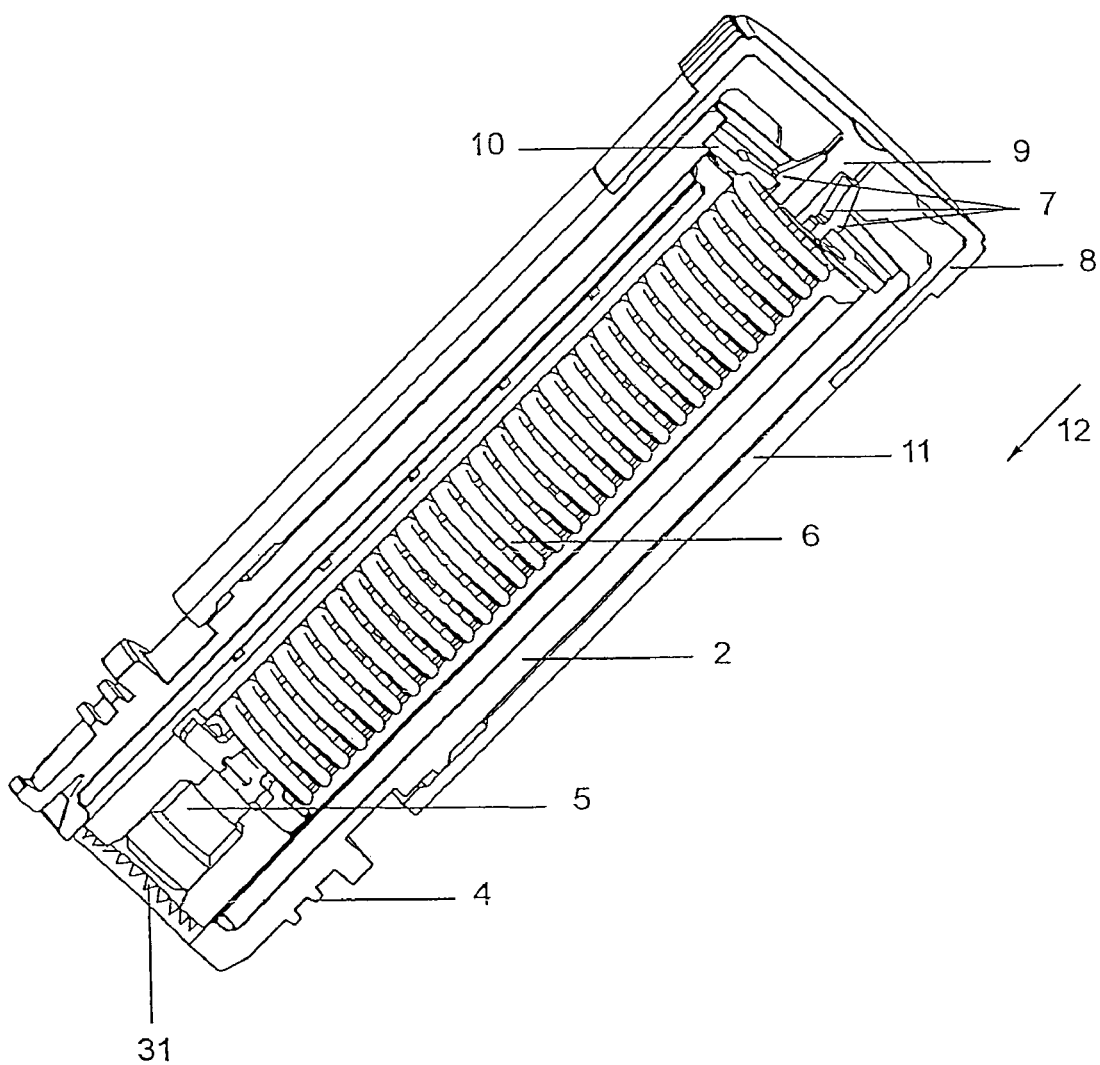
FIG. 2 is an enlarged sectional illustration of the activator part.

FIG. 1 depicts an injection device 1 whose housing is subdivided in the axial direction. The first housing part 2 encloses the activator part and the second housing part 3 encloses the injection part of the device according to the invention, the two housing parts being connectable by means of a thread 4. The activator part, which is illustrated in more detail in FIG. 2, comprises a pressure pin 5 that is axially displaceable within the housing 2 and insertable against a spring 6. The pressure pin 5 comprises inwardly resilient snap-in projections 7 forming the conical termination of the pressure pin 5. In the locked position, a pin 9 of a cap 8 keeps the snap-in projections 7 in a radially outwardly excursed position such that the snap-in connections 7 overlap the annular part 10. Upon removal of the cap 8, the activator part can be triggered by actuating the safety sleeve 11 in the sense of arrow 12, whereby the snap-in projections 7 are pressed inwardly and the pressure pin 5 is catapulted in the sense of arrow 12 by the force of the spring 6, thus causing the conical end formed by the snap-in projections 7 to pass through the clear cross section of the ring 10.

Figure 3:
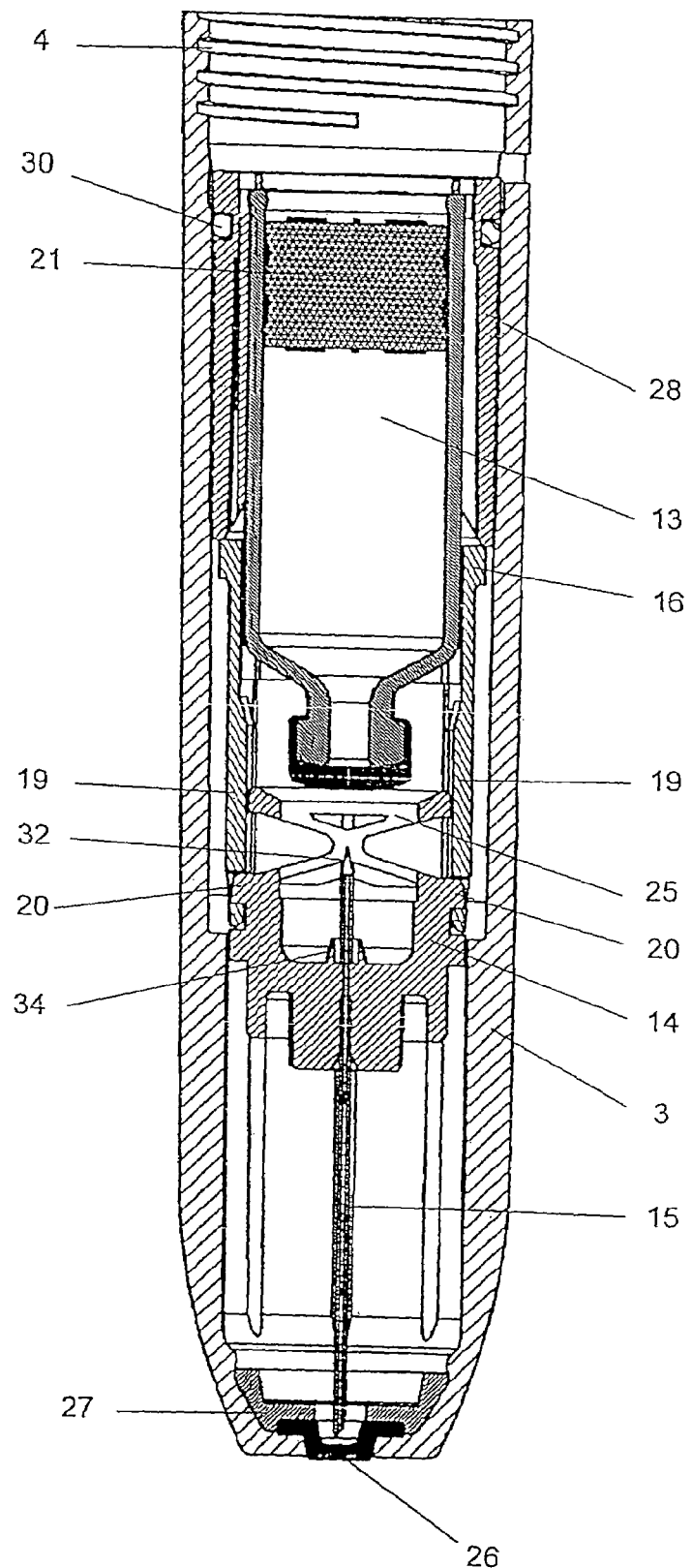
FIG. 3 is an enlarged illustration of the injector part.
Figure 4:
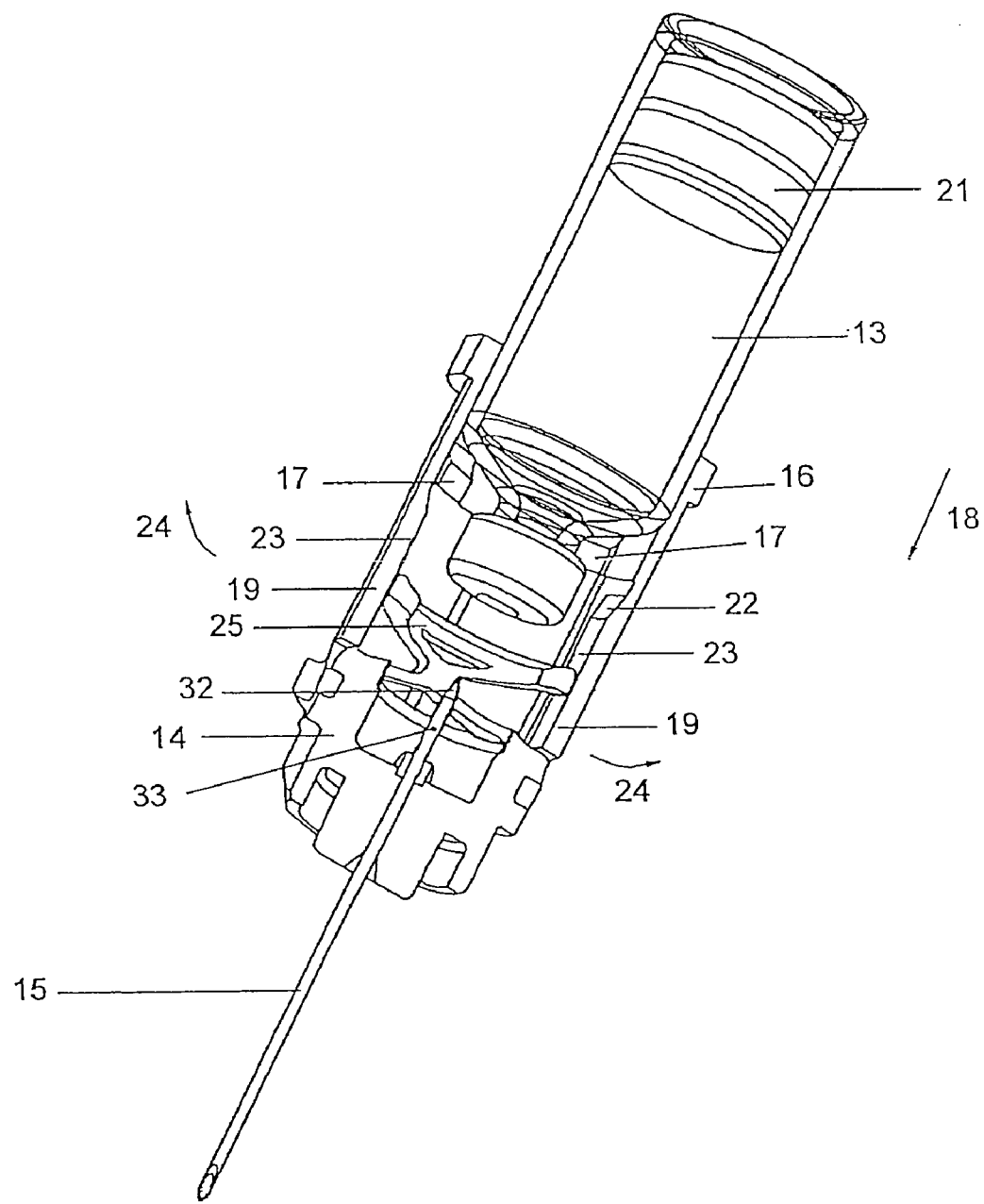
FIG. 4 is partially sectioned partial illustration of the injector unit.

FIG. 3 illustrates the injector part, in which an ampoule 13 and an injection needle 15 fixed in a needle guide 14 are mounted. The ampoule 13 in this case reaches into a sleeve 16 which is, in turn, secured against axial displacement in the housing 3. As is apparent from FIG. 4, the sleeve 16 on its inner periphery comprises radially inwardly protruding projections 17 defining a smaller diameter than the outer diameter of the ampoule 13. They are dimensioned such that the ampoule 13 rests on the wedge-shaped run-up surfaces of the projections 17. It is only under a strong mechanical action on the injector part occurring, for instance, as the latter is dropped from a great height, that an axial displacement of the ampoule 13 in the sense of arrow 18 is effected, which causes the ampoule 13 to be further displaced in the axial direction along the wedge-shaped run-up surfaces of the projections 17 under the expansion of the sleeve 16 and, consequently, be jammed between the projections 17, thus being secured against further axial displacement.

The sleeve 16 comprises radially outwardly resilient arms 19, which are provided with recesses into which respective snap-in noses 20 of the needle guide 14 engage. The needle guide 14 is thereby coupled to the sleeve 16 and likewise secured against axial displacement. It is only upon actuation of the injection device by triggering the pressure pin 5 that the needle guide will be released. The spring 6 of the activator part in this case is devised such that the pressure pin 5 exerts a force on the piston plug 21, thus causing a further displacement of the ampoule 13 in the sense of arrow 18 against the displacement resistance created by the projections 17. After this, the ampoule 13, via wedge-shaped run-up surfaces 22, impinges on projections 23 formed on the resilient arms 19 of the sleeve 16. This causes an excursion of the resilient arms 19 in the sense of arrows 24 such that the recesses will no longer be engaged from behind by the snap-in noses 20 and the needle guide 14 will be released.

Figure 5:
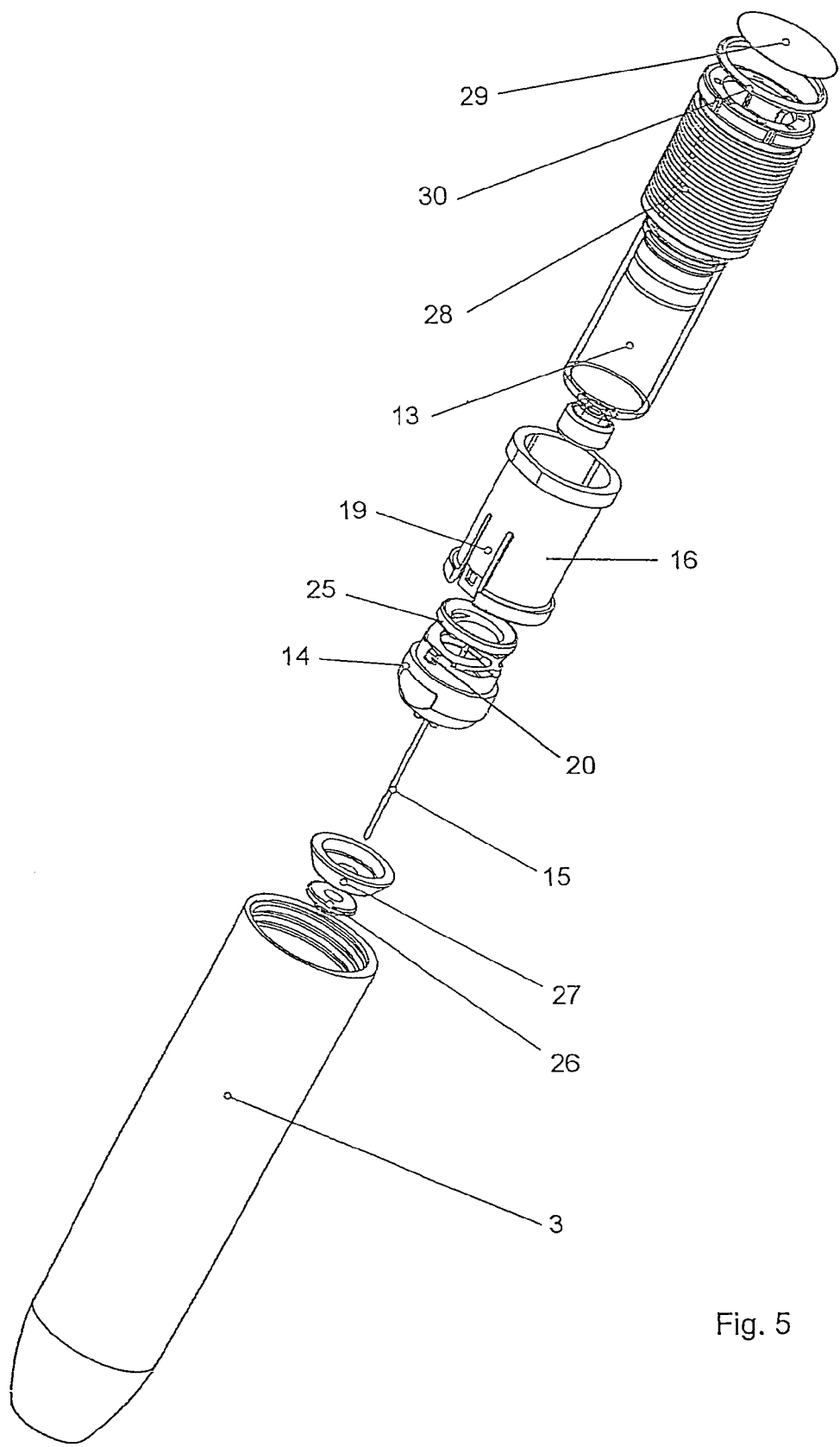
FIG. 5 is an exploded view of the injector part.
Figure 6:
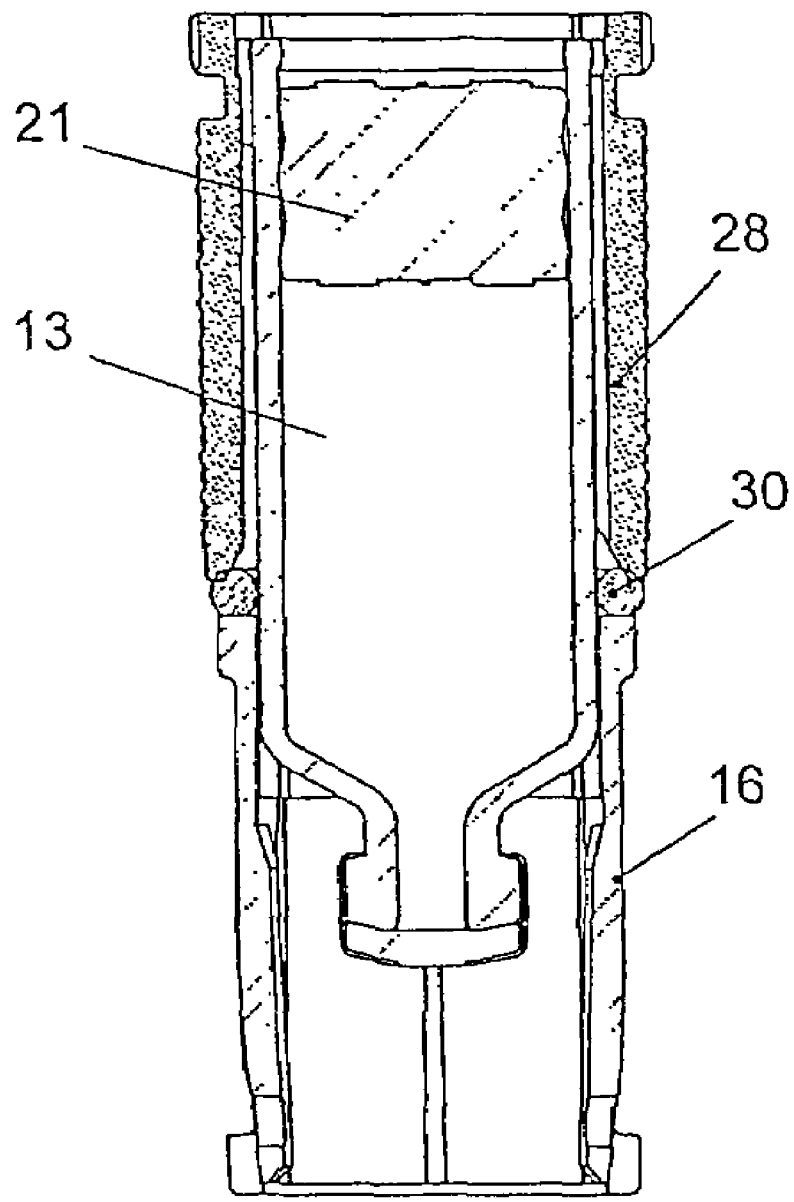
FIG. 6 shows a modified configuration of the injector part.

In order to dampen the impact of the ampoule 13 on the needle guide 14, a spring element and, in particular, a spring basket 25 is provided, which is formed in one piece with the needle guide 14. The ampoule 13 can subsequently be further moved on in the axial direction along with the needle guide 14, and the injection needle can emerge from the housing 3. From FIG. 3, it is apparent that the housing 3 is closed by a needle protection cap 26, which is held firmly in a clamping ring 27. From FIG. 3, it is further apparent that the ampoule 13 is retained in an ampoule socket 28, which protects the ampoule 13 against fracture. In the exploded view according to FIG. 5, the individual elements of the injector part are clearly illustrated, it being also apparent that the ampoule socket 28 is closed by a sealing foil 29 and sealed relative to the inner side of the housing 3 by a sealing ring 30. In this manner, the whole interior of the injector part is encapsulated so as to safeguard the permanent sterility of the injection unit including the ampoule. The sealing of the injector interior may, however, also be effected in another way, as illustrated in FIG. 6. There, the ampoule socket 28 on its outer periphery comprises a labyrinth seal which ensures the tightness of the ampoule socket relative to the housing 3. The labyrinth seal has a plurality of peripherally extending lamellas which are slit at a point along their peripheries, the slits of axially adjacent lamellas being each offset by 1800. The thus formed labyrinth is permeable for a gas that serves to sterilize the injector part so as to enable its introduction into the injector part through the labyrinth seal. The labyrinth seal, however, is impermeable to bacteria. Besides, the sealing ring 30 is to be seen, which, as opposed to the configuration according to FIG. 5, is not arranged between the ampoule socket 28 and the inner periphery of the housing 3, but between the ampoule socket 28 and the ampoule 13. With this configuration, a separate sealing disc is no longer necessary.

Figure 7A:
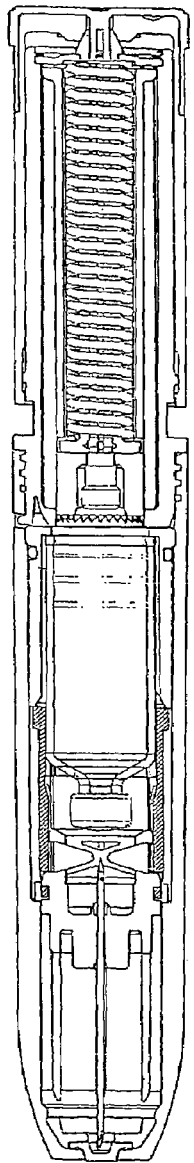
FIGS. 7a to 7h illustrate the operation sequence of the device according to the invention.
Figure 7B:
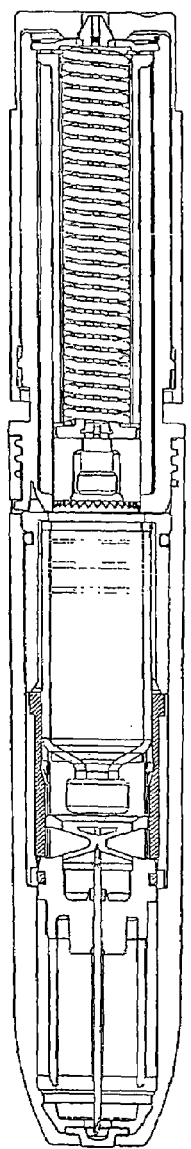
Figure 7C:
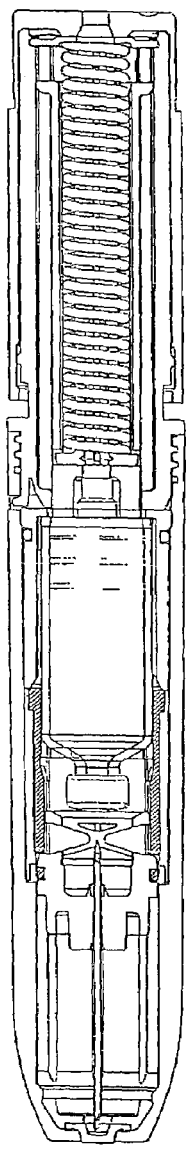
Figure 7D:
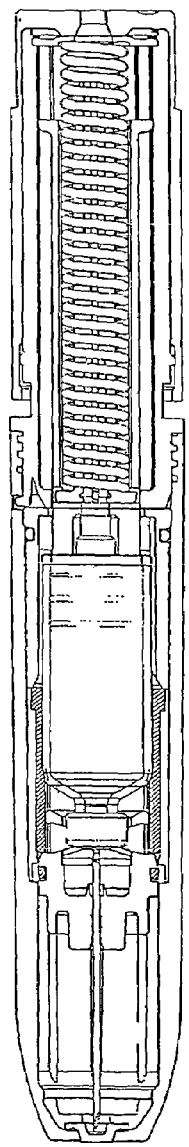
Figure 7E:
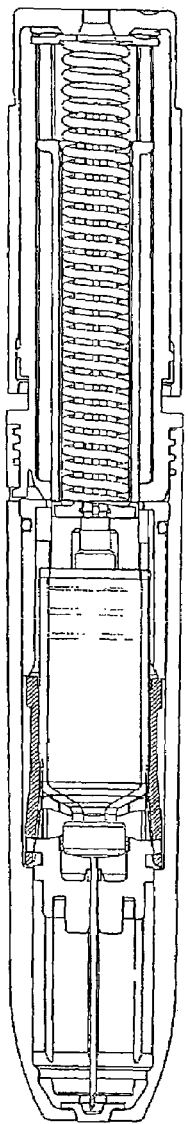
Figure 7F:
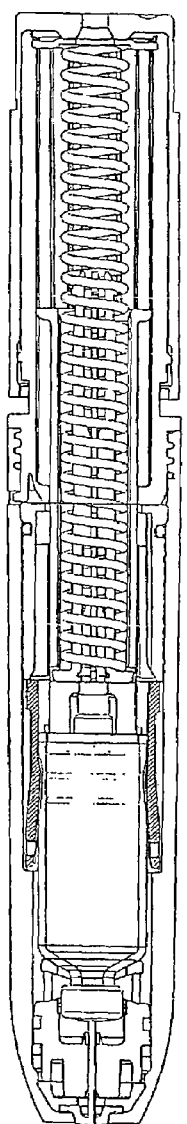
Figure 7G:
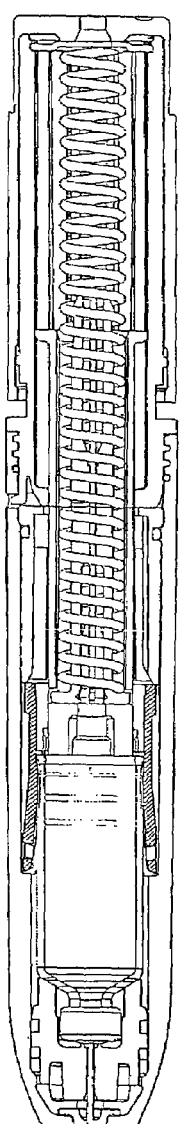
Figure 7H:
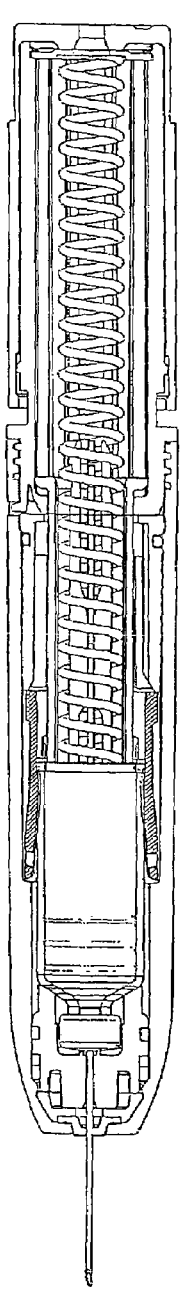

FIGS. 7a to 7h illustrate the operation sequence during the actuation of the injection device. FIG. 7a shows the starting position prior to the triggering of the activator. In FIG. 7b, the securing cap 8 has already been removed and the activator is triggered, with the snap-in projections 7 being compressed and the pressure pin 5 being released. In FIG. 7c, the pressure pin 5 extends, with the pressure pin end provided with a sprocket 31 punching the sealing foil 29. In FIG. 7d, the ampoule 13 is displaced forwardly in the axial direction against the displacement resistance exerted by the projections 17, running onto the projections 23 of the resilient arms 19. In FIG. 7e, the two spring arms 19 of the sleeve 16 are pivoted outwardly, thus releasing the needle guide 14. In FIG. 7f the ampoule-side injection needle end, which is designed as a perforation piece 32, pierces the needle protection cap of the ampoule 13. The ampoule is, thus, moved forwardly as far as to the end position along with the needle guide 14, with the injection needle 15 leaving the injection part with its full length. In FIG. 7g, the spring basket 25 is compressed while further displacing the ampoule 13 such that the injection needle 15 will pass completely through the sealing disc of the ampoule 13 and the radial opening 33 of the injection needle 15 will enter into communication with the injection liquid contained in the ampoule 13. At the same time, the annular web 34 illustrated in FIG. 3 penetrates the sealing disc of the ampoule 13, thus causing a closed annular space to form between the annular web 34 and the injection needle 15 reaching into the ampoule 13, which annular space prevents the injection liquid from leaving the ampoule 13 laterally outside of the injection needle 15. By enabling the injection liquid to emerge through the radial opening 33 and the injection needle 15, the piston plug 21 is driven forwardly as far as to the stop by the pressure pin 5 so as to cause all of the injection liquid to be ejected.

The invention claimed is:

1. A device for automatically injecting injection liquids, comprising an axially subdivided housing comprising at least two parts which are connectable with each other, wherein an axially displaceable pressure pin (5) is guided in a first housing part (2), which pin is capable of being inserted against a force accumulator (6) and locked in the inserted position and extended upon relief of the force accumulator (6), and an injection needle (15) fixed in a needle guide (14) and an ampoule (13) are mounted in a second housing part (3) so as to be axially displaceable relative to each other, wherein the injection needle (15) on its side facing the ampoule (13) is designed as a perforation piece for the ampoule (13), wherein the ampoule (13) with its end facing the injection needle (15) is mounted to reach into a sleeve (16) fixed within the second housing part (3), said sleeve (16) having an inner diameter that substantially corresponds to an outer diameter of the ampoule (13), radially inwardly protruding projections (17) are formed on an inner periphery of the sleeve (16), and the sleeve (16) comprises locking members cooperating with locking members (20) of the needle guide (14), whereby an axial displacement of the ampoule (13) in a direction toward the needle guide (14) while overcoming displacement resistance exerted by the projections (17) causes release of the locking members (20) and axial displaceability of the needle guide (14).

2. A device according to claim 1, wherein the locking members of the sleeve (16) are formed on arms (19) capable of moving outwardly in a resilient manner, said arms (19) each carrying an inwardly protruding projection (23) in a region of a coupling site of said arm (19), which projection (23) cooperates with the ampoule (13) under the movement of the arms (19) and release of the locking members (20).

3. A device according to claim 1, wherein an end-side annular surface of the sleeve (16) facing the needle guide (14) rests on a radially inwardly protruding projection of the second housing part (3).

4. A device according to claim 1, wherein the locking members of the needle guide (14) are snap-in noses (20) engaging in reception openings.

5. A device according to claim 1, wherein a spring element acting in an axial direction is arranged between the needle guide (14) and the ampoule (13).

6. A device according to claim 5, wherein the spring element is designed in one piece with the needle guide (14), as a spring basket (25) compressible in the axial direction.

7. A device according to claim 1, wherein the injection needle (15) comprises a radial passage opening (33) at an axial distance from its end designed as a perforation piece (32) for the ampoule (13).

8. A device according to claim 7, wherein the radial passage opening (33) in the axial direction is arranged between the injection needle end designed as a perforation piece (32) and an annular web (34) arranged on the needle guide (14) and surrounding the injection needle (15), said annular web (34) defining a closed annular space between the web (34) and the injection needle (15) reaching into the ampoule (13).

9. A device according to claim 1, wherein the ampoule (13) with its end facing away from the injection needle (15) is arranged to reach into a sleeve-shaped ampoule socket (28) which comprises a plurality of lamellar guide ribs extending in the longitudinal direction.

10. A device according to claim 8, wherein an ampoule reception opening facing the first housing part (2) including the pressure pin (5) is closed by a gas-permeable sealing foil (29).

11. A device according to claim 9, wherein a seal is arranged between an outer periphery of the ampoule socket (28) and an inner periphery of the second housing part (3).

12. A device according to claim 8, wherein an outer periphery of the ampoule socket (28) comprises a labyrinth seal, and a seal is arranged between the ampoule socket (28) and the ampoule (13).

13. A device according to claim 11, wherein the seal is an O-ring seal (30).

14. A device according to claim 12, wherein the seal arranged between the ampoule socket (28) and the ampoule (13) is an O-ring seal (30).

15. A device according to claim 2, wherein an end-side annular surface of the sleeve (16) facing the needle guide (14) rests on a radially inwardly protruding projection of the second housing part (3).

16. A device according to claim 2, wherein the locking members of the needle guide (14) are snap-in noses (20) engaging in reception openings.

17. A device according to claim 3, wherein the locking members of the needle guide (14) are snap-in noses (20) engaging in reception openings.

18. A device according to claim 2, wherein a spring element acting in an axial direction is arranged between the needle guide (14) and the ampoule (13).

19. A device according to claim 3, wherein a spring element acting in an axial direction is arranged between the needle guide (14) and the ampoule (13).

20. A device according to claim 4, wherein a spring element acting in an axial direction is arranged between the needle guide (14) and the ampoule (13).

* * * * *